(12) United States Patent
Kreindel et al.

(10) Patent No.: US 8,273,037 B2
(45) Date of Patent: Sep. 25, 2012

(54) METHOD AND SYSTEM FOR SOFT TISSUE DESTRUCTION

(75) Inventors: Michael Kreindel, Zichron Ya'acov (IL); Lion Flyash, Nazareth-illit (IL); Boris Vaynberg, Zichron Yaakov (IL)

(73) Assignee: Syneron Medical Ltd, Yokneam Illit (IL)

( * ) Notice: Subject to any disclaimer, the term of this patent is extended or adjusted under 35 U.S.C. 154(b) by 1193 days.

(21) Appl. No.: 12/076,524

(22) Filed: Mar. 19, 2008

(65) Prior Publication Data

US 2008/0234609 A1 Sep. 25, 2008

Related U.S. Application Data

(60) Provisional application No. 60/907,089, filed on Mar. 19, 2007.

(51) Int. Cl.
*A61H 7/00* (2006.01)

(52) U.S. Cl. ............................................. 601/6; 601/9

(58) Field of Classification Search ............ 601/2, 6–12, 601/46, 47; 602/13; 128/DIG. 20
See application file for complete search history.

(56) References Cited

U.S. PATENT DOCUMENTS

| | | | |
|---|---|---|---|
| 6,605,080 B1 * | 8/2003 | Altshuler et al. | 606/3 |
| 2006/0036300 A1 * | 2/2006 | Kreindel | 607/99 |
| 2008/0009885 A1 * | 1/2008 | Del Giglio | 606/128 |
| 2009/0076420 A1 * | 3/2009 | Kreindel | 601/2 |

* cited by examiner

*Primary Examiner* — Michael A. Brown
(74) *Attorney, Agent, or Firm* — Vorys, Sater, Seymour and Pease LLP; William L. Klima

(57) ABSTRACT

A method and system for adipose tissue treatment. The system of the invention includes an applicator configured to apply negative pressure pulses to a skin surface when activated by a controller, where the negative pressure is created during a time interval in which the flow of water through the cell membrane is not significant. An intensity of the negative pressure is used that causes selective damage to fat cells.

11 Claims, 5 Drawing Sheets

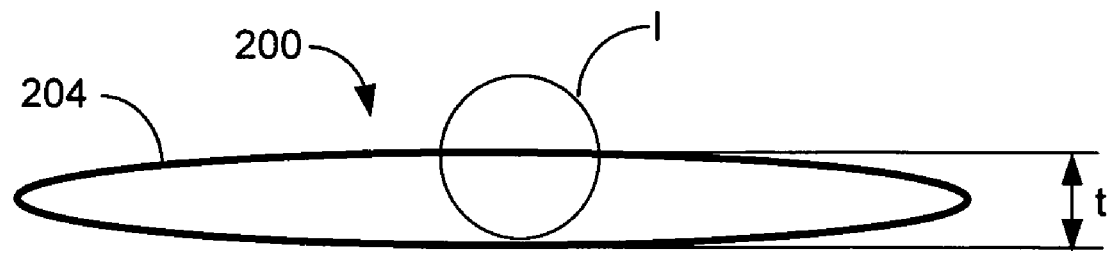
FIG5
VIEW I
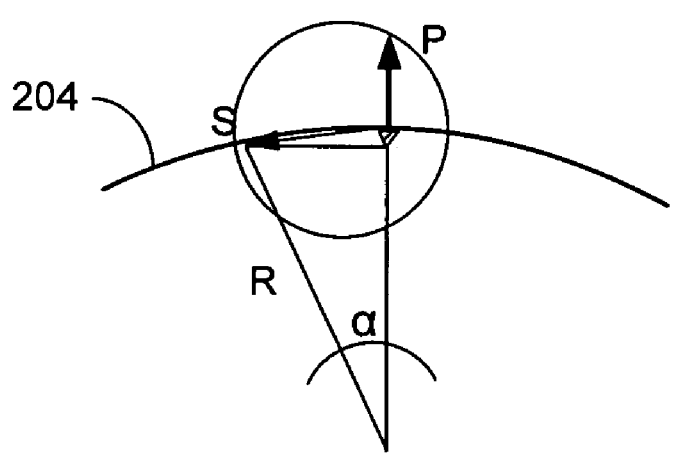

METHOD AND SYSTEM FOR SOFT TISSUE DESTRUCTION

CROSS-REFERENCE

This is a Non-Provisional Application of U.S. Provisional Patent Application Ser. No. 60/907,089, filed on Mar. 19, 2007, the entire content of which is hereby incorporated by reference in its entirety.

FIELD OF THE INVENTION

The method and device relate to medical devices and more specifically to devices and methods for adipose tissue treatment.

BACKGROUND OF THE INVENTION

When energy is applied to a skin surface in order to degrade subcutaneous adipose tissue, the energy should preferably reach the underlying adipose tissue layer without damaging the skin surface.

Various types of devices have been used for the treatment of adipose tissue. One popular method of fat treatment is liposuction. This is an invasive procedure involving mechanical disruption of the fat and subsequent removal of the resulting debris from the body. The main disadvantage of this method is its invasive character.

U.S. Pat. No. 5,143,063 describes a method for treating adipose tissue based on thermal destruction of fat by exposing adipose tissue to focused microwave or ultrasound waves. The intensity and the focusing of the energy are determined so as to selectively destroy fat cells without damaging the skin or deep tissues.

U.S. Pat. No. 6,113,558 discloses the delivery of high intensity focused ultrasound (HIFU) in pulsed mode for the treatment of such tissues as cancer tissues and blood clots.

US Published Patent Application US2004/0039312 discloses the application of HIFU for the destruction of adipose tissue. The destruction of the adipose tissue is mainly via hyperthermia.

U.S. Pat. No. 6,607,498 discloses HIFU pulsed to produce cavitation which selectively destroys fat cells.

U.S. Pat. No. 5,725,482 discloses superposition of ultrasound waves from two or more sources to create a wave having a high intensity localized at the adipose tissue to be treated.

U.S. Pat. No. 6,500,141 improves treatment safety with ultrasound by shaping the skin surface using suction.

U.S. Pat. No. 4,958,639 discloses destruction of calculi in the kidney using shock waves.

SUMMARY OF THE INVENTION

In one of its first aspects, the present invention provides a method for adipose tissue treatment comprising applying at least one negative pressure pulse to the skin surface, the negative pressure being created during a time interval in which flow of liquids through a cell membrane is not significant, and the intensity of the negative pressure causes selective damage to fat cells.

In another of its aspects, the invention provides a system for adipose tissue treatment comprising:
(a) a controller; and
(b) an applicator communicating with the controller, the applicator being configured to apply at least one negative pressure pulse to the skin surface when activated by the controller, the negative pressure being created during a time interval in which the flow of water through the cell membrane is not significant, and the intensity of the negative pressure causing selective damage to fat cells.

BRIEF LIST OF DRAWINGS

The disclosure is provided by way of non-limiting examples only, with reference to the accompanying drawings, wherein:

FIG. 5 is a schematic diagram of a force operating on a cell membrane.

DESCRIPTION OF EXEMPLARY EMBODIMENTS

Figure 1:
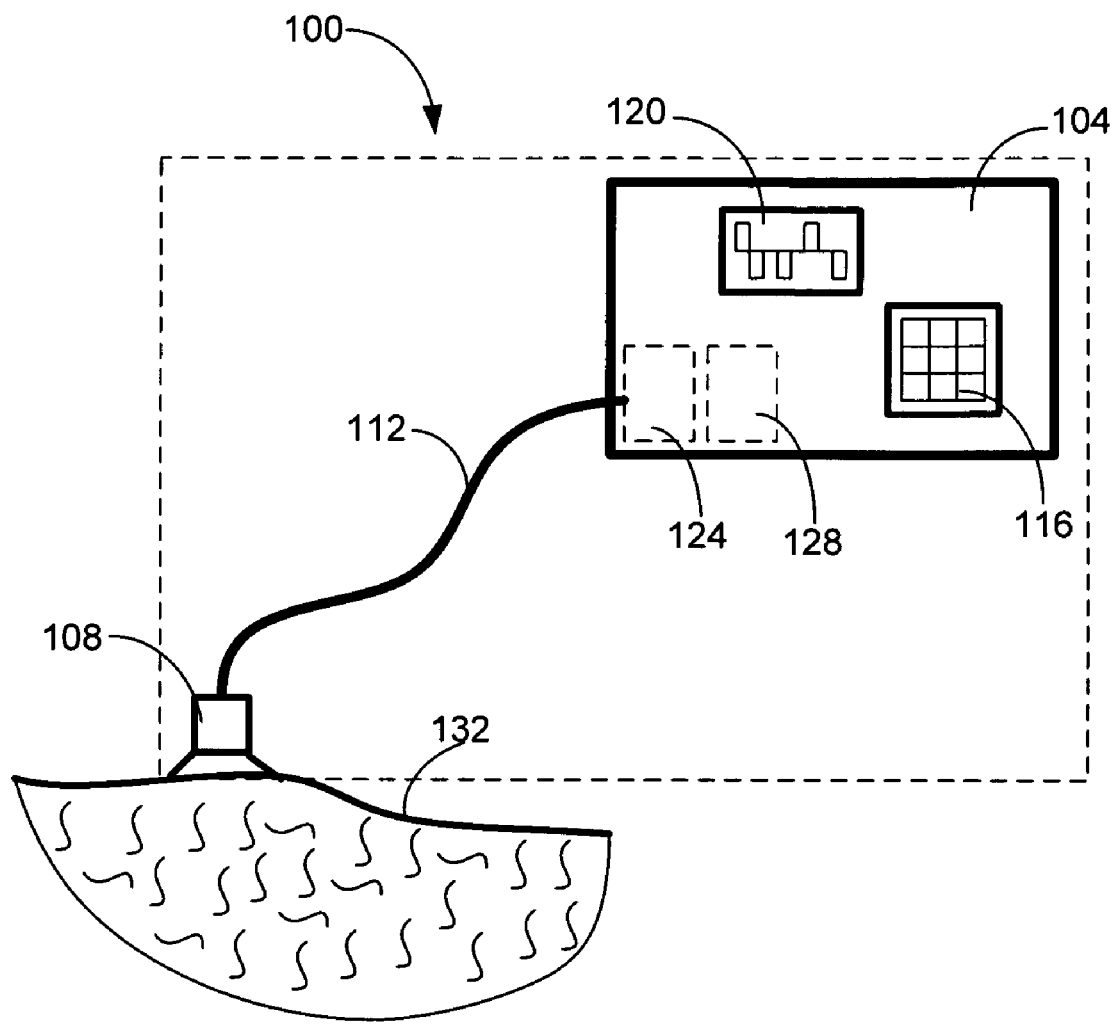
FIG. 1 is a schematic illustration of an exemplary embodiment of the present apparatus for treatment of adipose tissue.

The principles and execution of the method and apparatus described thereby may be understood with reference to the drawings, wherein like reference numerals denote like elements through the several views and the accompanying description of non-limiting, exemplary embodiments.

The present method and apparatus are for the treatment of soft tissue such as adipose tissue. In accordance with the present method, a pressure pulse having at least one negative pressure phase with respect to the ambient pressure is applied to a region of skin. As explained below, the intensity and time profile of the pressure pulse are selected to effect maximal destruction of fat cells with minimal damage to other tissues cells.

The present apparatus includes an applicator configured to be applied to the skin surface of a mammal and deliver a train of negative pressure pulses to the skin surface. The applicator has a chamber with an opening that is applied to the skin region to be treated when the applicator is applied to the skin surface. The air pressure in the chamber is transiently made to descend below the ambient atmospheric pressure in order to apply a negative pressure to the skin region to be treated. The applicator is connected to a controller configured to activate the applicator to deliver a train of negative pressure pulses to the skin surface. The frequency, intensity, and waveform are selectable by a user by means of one or more user input devices, such as a keypad, or touch screen.

FIG. 1 is a schematic illustration of an exemplary embodiment of the present apparatus for treatment of adipose tissue. Apparatus 100 includes a controller 104, an applicator 108 and a cable 112 enabling communication between controller 104 and applicator 108. Controller 104 is configured to activate applicator 108 to deliver a train of negative pressure pulses to the skin surface. A user may select the frequency, intensity, and waveform by means of one or more user input devices, such as a keypad 116, or touch screen 120. Controller 104 may include a source of vacuum such as a vacuum pump 124. Alternatively, controller 104 may include a source of pressurized fluid, or a pump/compressor 128 generating a flow or pressurized fluid. Applicator 108 is configured to be applied to skin surface 132 of a mammal and deliver a train of negative pressure pulses to skin surface 132. The term "fluid" as used in the present disclosure includes gas, air and liquid.

Figure 2:
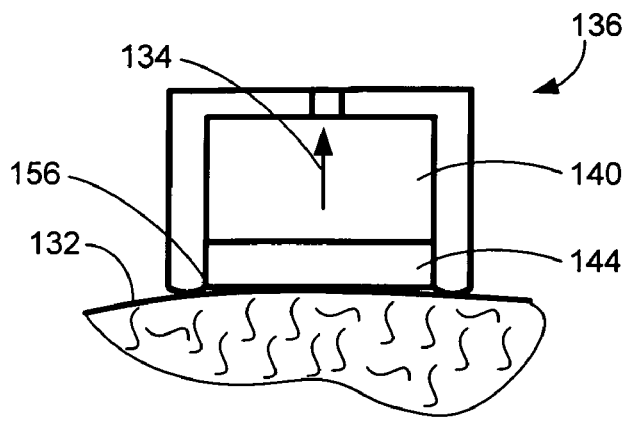
FIG. 2 is a schematic illustration of the principles of operation of the applicator for treatment of adipose tissue.
Figure 2:
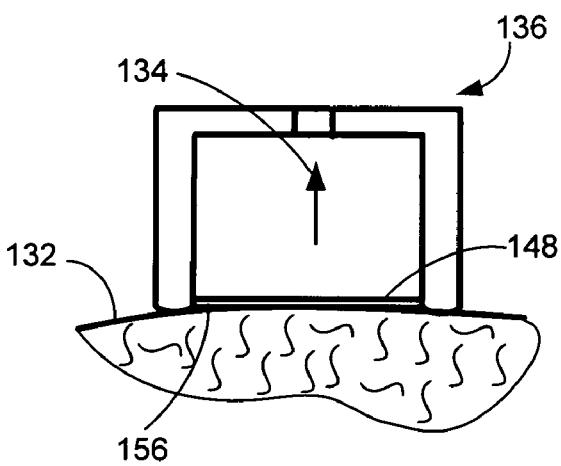
Figure 2:
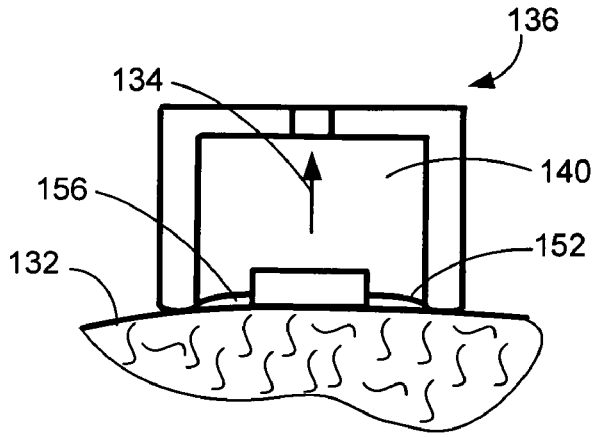

FIG. 2 is a schematic illustration of the principles of operation of the applicator for treatment of adipose tissue. Applicator 136 has a chamber 140 having an opening that is applied to a skin surface 132 to be treated when applicator 136 is applied to the skin surface 132. The air pressure in chamber 140 is transiently made to descend below the ambient atmospheric pressure. Applicator 136 contains a rigid plate 144 (FIG. 2A) or a flexible membrane 148 (FIG. 2B), or a combination of a rigid plate and a flexible membrane 152 (FIG. 2C) located in the interior of chamber 140. The plate or membrane is forced to rapidly move in chamber 140 away from skin surface 132, as indicated by arrow 134, in order to generate a negative pressure in the portion of the chamber 140 interior 156 between the surface of plate 144 and skin 132.

The plate or membrane may be coupled directly to the skin surface 132 to which the negative pressure pulse is applied. Alternatively, the plate or membrane may be coupled to the skin surface with the help of a coupling medium having acoustic properties similar to the treated tissue. For example, a water based gel, cream or oil based substance can be used as the coupling medium.

Figure 3:
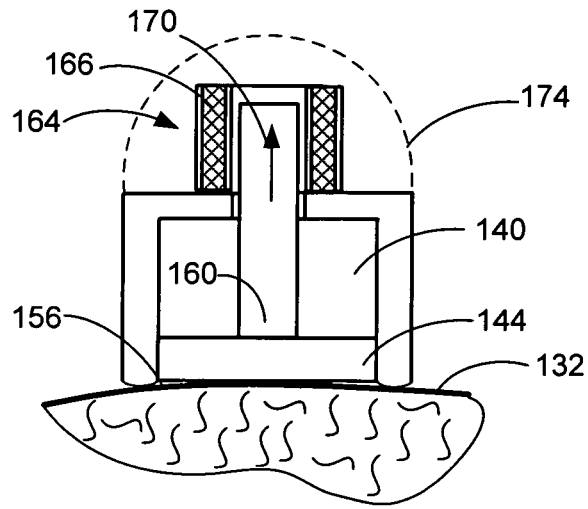
FIG. 3 is a schematic illustration of an exemplary embodiment of the applicator for treatment of adipose tissue.
Figure 3:
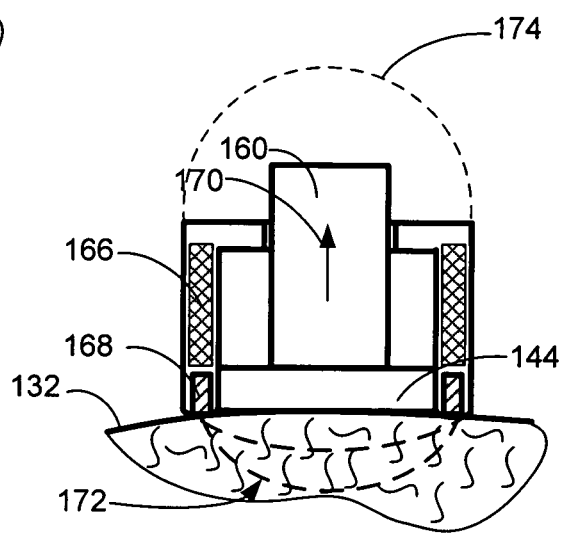
Figure 3:
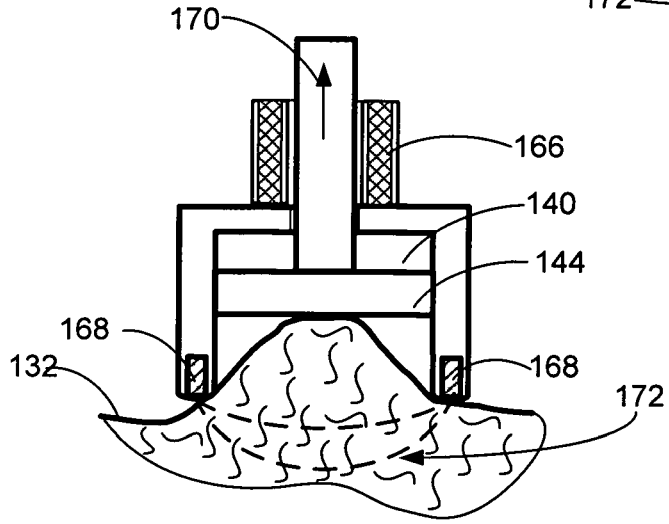

FIG. 3 is a schematic illustration of an exemplary embodiment of the applicator for treatment of adipose tissue. The movement of plate 144 or membrane 148 or a combination of them 152 (FIG. 2) may be generated by any method. For example, solid plate 144 may be attached to shaft 160 of a solenoid 164 to form a piston that can slide in the interior of chamber 140 (FIG. 3A). When an electrical current flows in the coil 166 of solenoid 164, the piston moves away from the skin surface as shown by arrow 170, and thus creates a negative pressure in the interior of chamber 140 (and particularly in the volume located between the plate 144 and skin 132). This negative pressure or vacuum causes the skin surface 132 adjacent to the chamber opening to protrude into the chamber 140 (FIG. 3B). A pair of RF electrodes 168 may be located in the applicator. An RF current can then be applied to the protruding skin surface 132 from electrodes 168. Numeral 174 marks a safety arrangement schematically shown in phantom lines as a cupola protecting the space required for solenoid shaft sliding. Numeral 172 indicates RF induced current lines heating the tissue between electrodes 168.

FIG. 3C illustrates an additional embodiment of a solenoid driven plate 144. Solenoid coil 166 may be mounted in the body of chamber 140 operating directly on made from a suitable material plate 144 that can be a magnetic material, and specially adapted shaft 160.

Alternatively, plate 144 only may be from a magnetizable (ferromagnetic) material, such as a metal, in which case plate 144 movement may be generated using a magnetic actuator that generates a force pulling plate 144 or membrane 148 away from the skin 132 surface generating a negative pressure in interior 156 between the surface of plate 144 and skin 132. Shaft 160 in such case serves merely as a guide shaft.

In yet another alternative (not shown), a first coil may be attached to the plate or membrane and a second plate or membrane positioned adjacent to the first coil, but not attached to the plate or membrane. The pair of coils is driven with a current pulse. According to the relative polarity of the current in the two coils, a push or pull force is generated on the plate or membrane.

Figure 4:
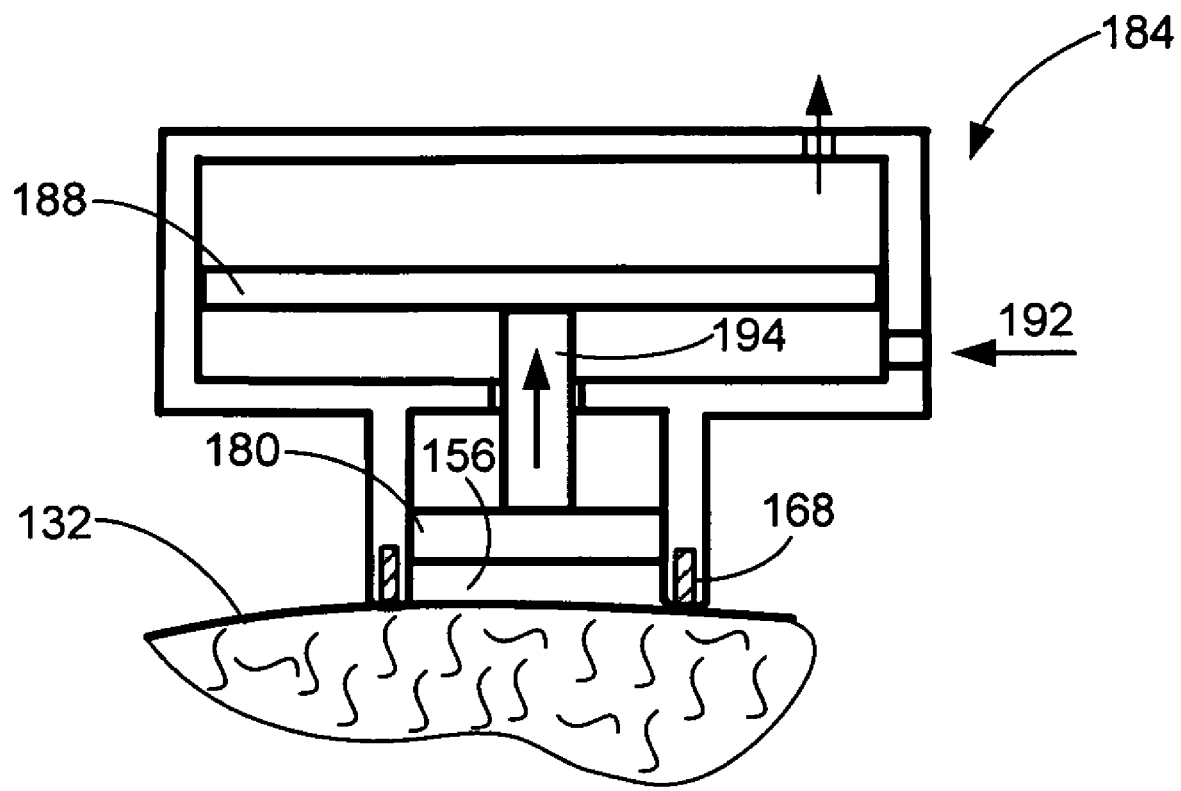
FIG. 4 is a schematic illustration of another exemplary embodiment of the applicator for treatment of adipose tissue.

FIG. 4 is a schematic illustration of another exemplary embodiment of the applicator for treatment of adipose tissue. This embodiment is based on fluid actuators, which produce an outward force pulling plate 180 of applicator 184 by controlled application of compressed pressure fluid pulses generating negative pressure pulses (vacuum pulses) in interior 156 between the surface of plate 180 and skin 132. Compressed fluid supply shown by arrow 192 may be provided by an optional compressed fluid source 128 of controller 104 (FIG. 1). There is no need for a high-pressure compressed fluid source. The difference in the surface area of plate 180 and piston 188 rigidly connected by shaft 194 to plate 180 may be made sufficient enough to amplify the force developed by compressed fluid 192. A pair of RF electrodes 168 may be located in applicator 184. An RF current can then be applied to the protruding skin surface 132 from the electrodes 168.

A pressure pulse repetition rate may be used that is typically between 1 to 1000 pulses per second, although a test conducted in the range of 1 to 50 and 1 to 100 pulses per second indicate positive results. It has been found that application of negative pressure pulses to the skin surface in this frequency range causes destruction of fat cells, with little or no damage to other tissues. Without wishing to be bound by a particular theory, it is believed that the negative pressure pulls the tissue to be treated outwards from the body, causing strain in the tissue cells which disrupts the tissue cells. In particular, since fat cells are larger and weaker than other cells, the pulse rate and pulse amplitude may be selected to selectively destroy fat cells.

An outwardly directed external pressure on the fat cell membrane creates strong pressure on the cell membrane. This pressure difference is counteracted by the strength of the membrane. FIG. 5 shows a force diagram on a fat cell 200 membrane 204, in which:

P is the difference between the inwardly directed pressure acting on the membrane by the cell interior and the outwardly directed pressure applied by the applicator of the present invention on the cell membrane.

S is the lateral strength of membrane elements.

$\alpha$ is an angle subtended by a membrane element.

R is a radius of the cell.

t is the thickness of an adipose tissue cell.

The external pressure in a radially outward direction should be compensated by the strength between the elements.

Assuming a mosaic model of membrane structure (each element has 6 neighbors), $$P = 6 S_R \tag{1}$$

The projection of the force in the radially inward direction ($S_R$) can be estimated for small angle ($\alpha$) as follows:

$$S_R = S \frac{t}{R}. \tag{2}$$

Thus, the surface strength can be estimated as:

$$S = \frac{PR}{6t} \tag{3}$$

For a large fat cell P would be equal to $5 \times 10^4$ Atm, the cell radius would be about $5 \times 10^{-5}$ m and cell thickness about $5 \times 10^{-9}$ m, which leads to:

$$S = \frac{5 \cdot 10^4 \cdot 5 \cdot 10^{-5}}{6 \cdot 5 \cdot 10^{-9}} = 8.5 \cdot 10^7 Pa = 850 \text{ Atm} \tag{4}$$

Thus, a radially outward force exceeding 850 Atm is necessary to rupture the membrane. Equation (3) shows that the larger the cell radius, the stronger the strength of the membrane. For cells having a radius of 5 microns, the strength will be 20 times lower than for a fat cell having a radius of 100 microns. The treatment of the present method enables a selectivity mechanism that destroys fat tissue over other tissues.

The rise time of the negative pressure pulse should preferably be shorter than diffusion time of water and fat through the cell membrane. This is because with a longer rise time, the net outward pressure balance would be reduced by fluid flows inside the cell. (Typical diffusion times of water are 3 to 20 millisecond. Source "Time dependent water diffusion in a biological model system" *Proc. Natl. Acad. Sci. Vol.* 91, pp 1229-1233, February 2004, *Biophysics*) This effect might occur if the fat cell content behaves as a low viscosity liquid. At low temperatures, the fat may have a very high viscosity and then flow of the fat inside the cell would be much less significant. Increasing the tissue temperature reduces the viscosity and preheating tissue prior to applying the pulse of negative pressure can improve efficiency of the treatment significantly.

Therefore, in accordance with another embodiment of the method, prior to and/or simultaneously with the application of the pressure pulse, the adipose tissue is heated to an elevated temperature, which is lower than the damage temperature, but higher than normal body tissue temperature. (It is well known that the tissue damage temperature is 44 degrees Celsius.)

In accordance with the present method the following types of skin heating can be applied:
   RF current driven into the tissue via at least one electrode touching the skin.
   Electromagnetic power radiated on the tissue in the visible, infrared or microwave range.
   High intensity ultrasound energy.

Preferably the heating is space selective. Namely, it is focused on specific zones where the desired cell destruction is to occur. Preferably, the heating is applied to a depth of at least 3 mm, below the skin surface, where the adipose tissue is located. In another embodiment, cooling means are applied to the skin surface to further reduce unwanted damage to skin layers.

While the exemplary embodiments of the method and apparatus for destroying fat tissue have been illustrated and described, it will be appreciated that various changes can be made therein without affecting the spirit and scope of the method. The scope of the method, therefore, is defined by reference to the following claims:

What is claimed is:

1. A method for adipose tissue treatment comprising applying at least one negative pressure pulse to the skin surface, the negative pressure being created during a time interval in which flow of liquids through a cell membrane is not significant, and the intensity of the negative pressure causes selective damage to fat cells.

2. The method according to claim 1 wherein the time interval is at least 3 millisecond.

3. The method according to claim 1 wherein significant damage to other tissues does not occur.

4. The method according to claim 1 wherein the pressure pulse is generated by a solenoid.

5. The method according to claim 1 wherein the pressure pulse is generated using compressed fluid.

6. The method according to claim 1 wherein pressure pulse is created by vacuum pump.

7. The method according to claim 1 wherein tissue heating is applied prior to the pulse of negative pressure.

8. The method according to claim 1 wherein tissue heating is applied essentially simultaneously with the pulse of negative pressure.

9. The method according to claim 6 wherein the heat source is an RF current.

10. The method according to claim 6 wherein the heat is generated from electromagnetic energy.

11. The method according to claim 6 wherein heat is generated from ultrasound acoustic energy.

\* \* \* \* \*